United States Patent
Condie et al.

(10) Patent No.: US 9,814,523 B2
(45) Date of Patent: Nov. 14, 2017

(54) MULTIPOLARITY EPICARDIAL RADIOFREQUENCY ABLATION

(71) Applicant: Medtronic Ablation Frontiers LLC, Minneapolis, MN (US)

(72) Inventors: Catherine R. Condie, Shoreview, MN (US); Sarah E. Ahlberg, Crystal, MN (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 546 days.

(21) Appl. No.: 14/304,334

(22) Filed: Jun. 13, 2014

(65) Prior Publication Data
US 2014/0296850 A1 Oct. 2, 2014

Related U.S. Application Data

(62) Division of application No. 12/984,675, filed on Jan. 5, 2011, now Pat. No. 9,044,245.

(51) Int. Cl.
*A61B 18/14* (2006.01)
*A61B 18/00* (2006.01)

(52) U.S. Cl.
CPC ............ *A61B 18/1492* (2013.01); *A61B 2018/00029* (2013.01); *A61B 2018/00267* (2013.01); *A61B 2018/00363* (2013.01); *A61B 2018/00577* (2013.01); *A61B 2018/00821* (2013.01); *A61B 2018/1407* (2013.01); *A61B 2018/1467* (2013.01); *A61B 2218/002* (2013.01)

(58) Field of Classification Search
CPC ...... A61B 18/1492; A61B 2018/00577; A61B 2018/1467; A61B 2018/00363

USPC ..................................................... 606/32, 41
See application file for complete search history.

(56) References Cited

U.S. PATENT DOCUMENTS

| | | | |
|---|---|---|---|
| 5,366,443 A | 11/1994 | Eggers et al. | |
| 5,599,346 A | 2/1997 | Edwards et al. | |
| 5,681,282 A | 10/1997 | Eggers et al. | |
| 5,810,802 A * | 9/1998 | Panescu ............... | A61B 5/0422 374/E1.005 |
| 6,059,778 A * | 5/2000 | Sherman ............ | A61B 18/1206 606/34 |
| 6,200,314 B1 | 3/2001 | Sherman | |
| 6,955,675 B2 | 10/2005 | Jain | |

(Continued)

FOREIGN PATENT DOCUMENTS

EP 1977706 A1 10/2008

OTHER PUBLICATIONS

International Search Report and Written Opinion dated Mar. 29, 2012 for International Application Serial No. PCT/US2011/066468, International Filing Date: Dec. 21, 2011 consisting of 11 pages.

*Primary Examiner* — Jaymi Della
(74) *Attorney, Agent, or Firm* — Christopher & Weisberg, P.A.

(57) ABSTRACT

A method of ablating an epicardial tissue region, including positioning a medical device adjacent the epicardial tissue region, the medical device having a first electrode, a second electrode, and a third electrode located in between the first and second electrodes; delivering an irrigation fluid to the tissue region; and ablating at least a portion of the tissue region by sequentially activating the third electrode in a monopolar radiofrequency delivery mode and activating the first and second electrodes in a bipolar radiofrequency delivery mode.

9 Claims, 5 Drawing Sheets

(56) References Cited

U.S. PATENT DOCUMENTS

| | | | |
|---|---|---|---|
| 7,261,709 B2 | 8/2007 | Swoyer et al. | |
| 7,419,477 B2 * | 9/2008 | Simpson | A61M 25/0041 600/585 |
| 7,520,877 B2 | 4/2009 | Lee, Jr. et al. | |
| 7,648,499 B2 | 1/2010 | Orszulak et al. | |
| 7,706,894 B2 | 4/2010 | Stewart et al. | |
| 7,758,576 B2 | 7/2010 | Rothstein et al. | |
| 2002/0123749 A1 * | 9/2002 | Jain | A61B 18/1492 606/41 |
| 2002/0161361 A1 * | 10/2002 | Sherman | A61B 18/1206 606/34 |
| 2004/0162556 A1 * | 8/2004 | Swanson | A61B 18/1482 606/49 |
| 2005/0010095 A1 | 1/2005 | Stewart et al. | |
| 2007/0021745 A1 * | 1/2007 | McIntyre | A61B 18/1477 606/41 |
| 2007/0083193 A1 * | 4/2007 | Werneth | A61B 5/0422 606/41 |
| 2007/0083194 A1 * | 4/2007 | Kunis | A61B 18/1492 606/41 |
| 2008/0161803 A1 * | 7/2008 | Oral | A61B 18/1492 606/41 |
| 2008/0281312 A1 | 11/2008 | Werneth et al. | |
| 2008/0281322 A1 * | 11/2008 | Sherman | A61B 18/1492 606/42 |
| 2010/0057074 A1 * | 3/2010 | Roman | A61B 18/1492 606/33 |
| 2010/0125269 A1 * | 5/2010 | Emmons | A61B 18/1815 606/33 |
| 2010/0274238 A1 * | 10/2010 | Klimovitch | A61B 18/1442 606/33 |
| 2011/0010674 A1 | 1/2011 | Knize et al. | |
| 2012/0220999 A1 * | 8/2012 | Long | A61B 18/1206 606/41 |
| 2013/0296844 A1 * | 11/2013 | Werneth | A61B 18/1492 606/33 |
| 2014/0025069 A1 * | 1/2014 | Willard | A61B 18/1492 606/41 |

* cited by examiner

MULTIPOLARITY EPICARDIAL RADIOFREQUENCY ABLATION

CROSS-REFERENCE TO RELATED APPLICATION

This application is a divisional of patent application Ser. No. 12/984,675, filed Jan. 5, 2011, entitled MULTIPOLARITY EPICARDIAL RADIOFREQUENCY ABLATION, the entirety of which is incorporated herein by reference.

STATEMENT REGARDING FEDERALLY SPONSORED RESEARCH OR DEVELOPMENT n/a

FIELD OF THE INVENTION

The present invention relates to medical devices and methods of use thereof, and in particular towards medical devices for the thermal treatment of tissue.

BACKGROUND OF THE INVENTION

Minimally invasive devices are often employed for medical procedures, including those involving ablation, dilation, and the like. In a particular situation, an ablation procedure may involve creating a series of inter-connecting or otherwise continuous lesions in order to electrically isolate tissue believed to be the source of an arrhythmia. Such lesions may be created using a variety of different energy transmission modalities, such as cryogenic freezing or heating with radiofrequency ("RF") energy, for example.

Catheters or devices using cryogenic cooling may be used to lower the temperature of tissue, such as cardiac wall tissue, to an extent such that signal generation or conduction temporarily ceases and allows one to map or confirm that the catheter is positioned at a particular lesion or arrhythmia conduction site. Cryocatheters may also operate at lower temperatures for ablation treatment, e.g., to cool the tissue to a level at which freezing destroys the viability of the tissue, and, in the case of cardiac tissue, permanently removes it as a signal generating or signal conducting locus. Electrically driven RF ablation catheters typically include an arrangement of electrodes configured to contact tissue and apply RF energy thereto so that the tissue heats up due to resistive heating, creating an ablation lesion.

Irrespective of the particular ablation modality employed, the treatment goal common to virtually all cardiac or other ablation treatments is to create an effective lesion and/or provide for the desired, controlled destruction of selected tissues. Whether or not a particular treatment is successful may depend greatly on the qualities or characteristics of the lesion, such as its depth, uniformity, location, or the like. For example, for a cardiac arrhythmia, a particular lesion depth may be required to effectively obstruct the unwanted signal transmission through the problematic tissue region.

Existing therapeutic approaches are often limited in their range of operation, which may necessitate lengthy treatment procedures involving many iterations of ablative lesion forming, and re-mapping or checking the quality of lesion or symptomatic presence prior to completing a treatment procedure. Such steps may require an extended amount of time to perform, thus exposing the patient to undesired risk.

Accordingly, there remains a need for medical devices and methods that achieve an extended range of thermal transfer while ablating tissue more effectively and to a greater depth.

SUMMARY OF THE INVENTION

The present invention advantageously provides a method and system for achieving an extended range of thermal transfer while ablating tissue more effectively and to a greater depth. For example, a method of treating a tissue region is provided, including positioning a first, second, and third electrode in proximity to the tissue region, the second and third electrodes positioned on opposite sides of the first electrode; ablating at least a portion of the tissue region by conducting an electrical current between the first electrode and a ground electrode spaced from the tissue region; and ablating at least a portion of the tissue region by conducting an electrical current between the second electrode and the third electrode. The first, second, and third electrodes may be arranged in a substantially linear configuration on a medical device; may be arranged in a substantially arcuate configuration on a medical device; may be arranged side-by-side in a substantially parallel configuration; or may be arranged in a substantially concentric configuration. The method may include delivering a radiofrequency signal from a radiofrequency signal generator to the first electrode; measuring a temperature of at least one of the first, second, and third electrodes; and/or modifying the delivery of the radiofrequency signal based at least in part on the measured temperature. The tissue region may include an epicardial surface of a heart or a septal wall.

A method of ablating an epicardial tissue region is provided, including positioning a medical device adjacent the epicardial tissue region, the medical device having a first electrode, a second electrode, and a third electrode located substantially between the first and second electrodes; ablating at least a portion of the tissue region by conducting a radiofrequency signal between the third electrode and a return electrode located away from the epicardial tissue region; and ablating at least a portion of the tissue region by conducting a radiofrequency signal between the first and second electrodes. The method may include routing at least a portion of the medical device through a sub-xiphoid incision or through a thoracotomy incision; and/or re-positioning the medical device and operating the first, second, and third electrodes to create a plurality of ablative lesions. The method may include irrigating at least a portion of the first, second, and third electrodes.

A method of ablating an epicardial tissue region is provided, including positioning a medical device adjacent the epicardial tissue region, the medical device having a first electrode, a second electrode, and a third electrode located in between the first and second electrodes; delivering an irrigation fluid to the tissue region; and ablating at least a portion of the tissue region by sequentially activating the third electrode in a monopolar radiofrequency delivery mode and activating the first and second electrodes in a bipolar radiofrequency delivery mode. The method may include measuring an electrical activity of the epicardial tissue region.

A method of treating tissue is also provided, including ablating a first tissue region with a first portion of a medical device; and ablating a second tissue region with a second portion of the medical device, the second region substantially surrounding the first tissue region. Ablating the first tissue region may include conducting an electrical current between the medical device and a return electrode separate from the medical device, and ablating the second tissue region may include conducting an electrical current between two portions of the medical device.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
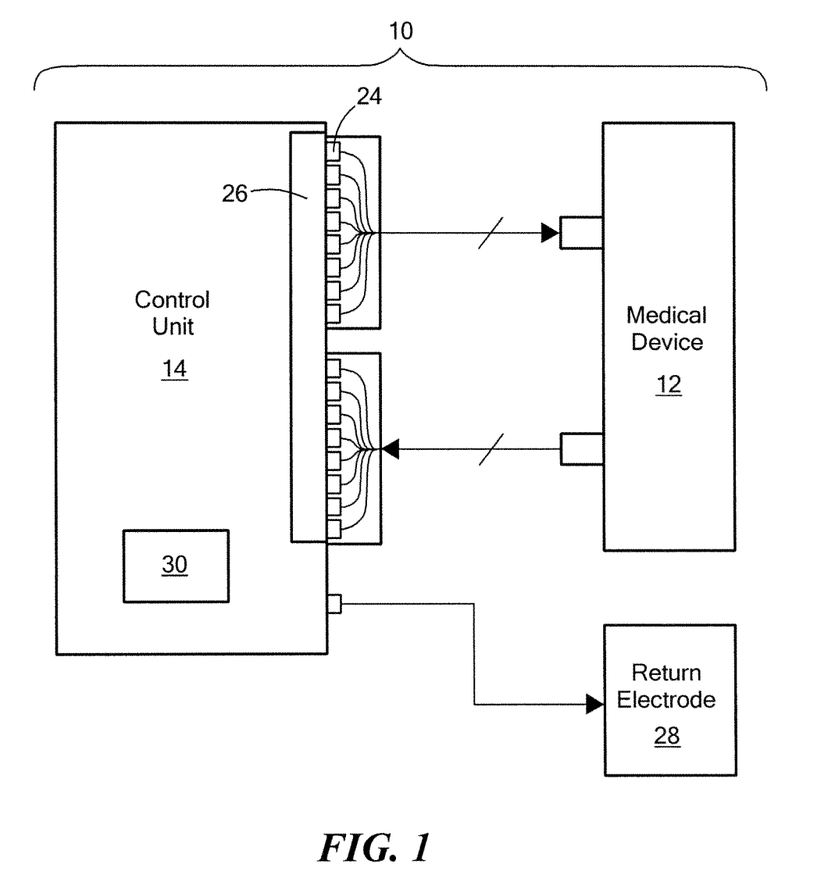
FIG. 1 is an illustration of an example of a medical system constructed in accordance with principles of the present invention.

The present invention advantageously provides a system and methods of use thereof for achieving an extended range of thermal transfer while ablating tissue more effectively and to a greater depth. Referring now to the drawing figures in which like reference designations refer to like elements, an embodiment of a medical system constructed in accordance with principles of the present invention is shown in FIG. 1 and generally designated as "10." The system 10 generally includes a medical device 12 that may be coupled to a control unit 14 or operating console.

Referring now to FIGS. 2-6, the medical device 12 may include an elongate body 16 passable through a patient's vasculature and/or insertable through a minimally invasive opening proximate to a targeted tissue region for diagnosis or treatment. The elongate body 16 may define a proximal portion (not shown) having a handle or other controllable implement accessible to an end-user. The medical device 12 may also include a distal portion 18 having one or more diagnostic or treatment assemblies for energetic, therapeutic and/or investigatory interaction between the medical device 12 and a tissue treatment site of a patient. The elongate body 16 may include one or more lumens disposed within that provide mechanical, electrical, and/or fluid communication between the proximal portion and the distal portion 18 of the elongate body 16.

Figure 2:
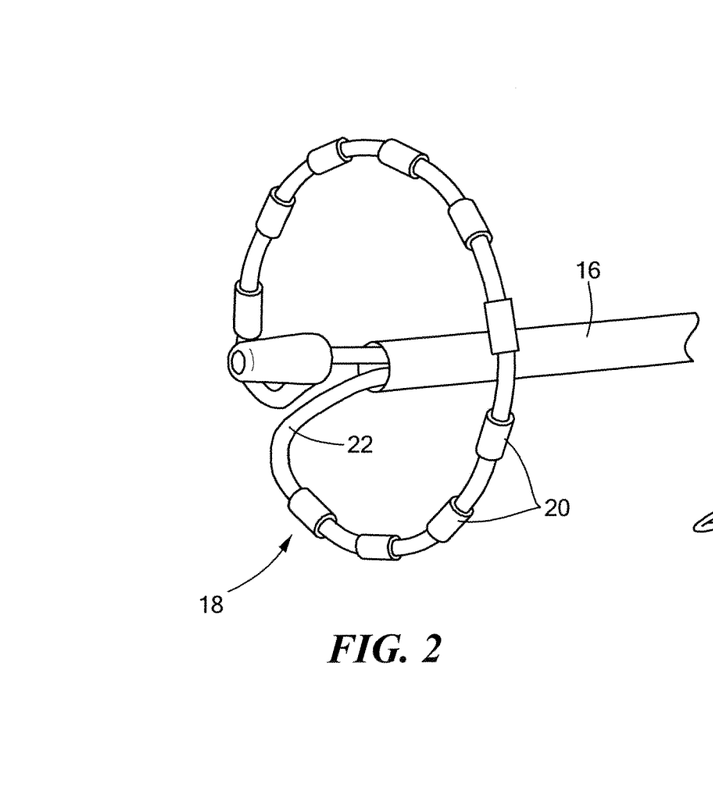
FIG. 2 is an illustration of an example of an electrode configuration for use with the medical system of FIG. 1.
Figure 3:
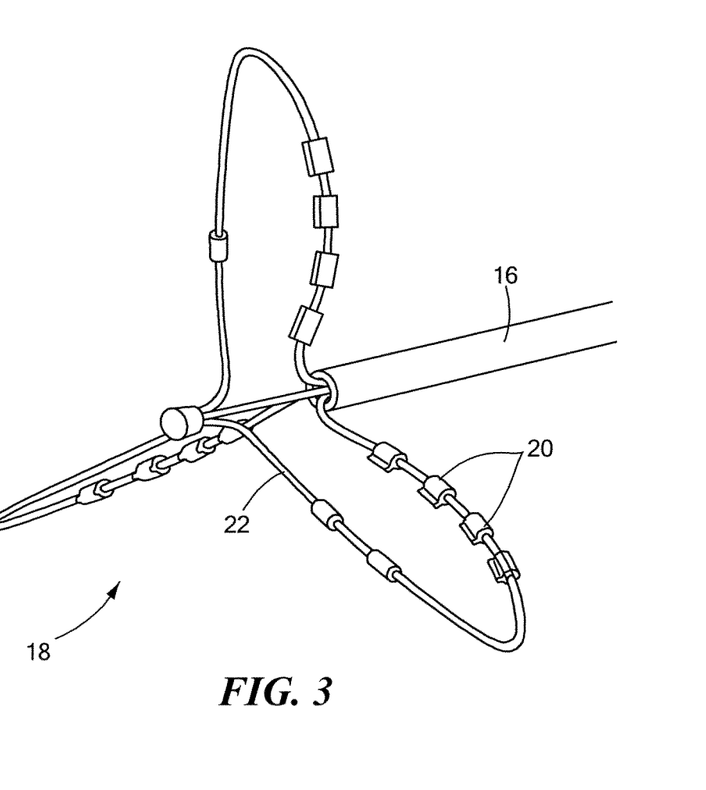
FIG. 3 is an illustration of another example of an electrode configuration for use with the medical system of FIG. 1.
Figure 4:
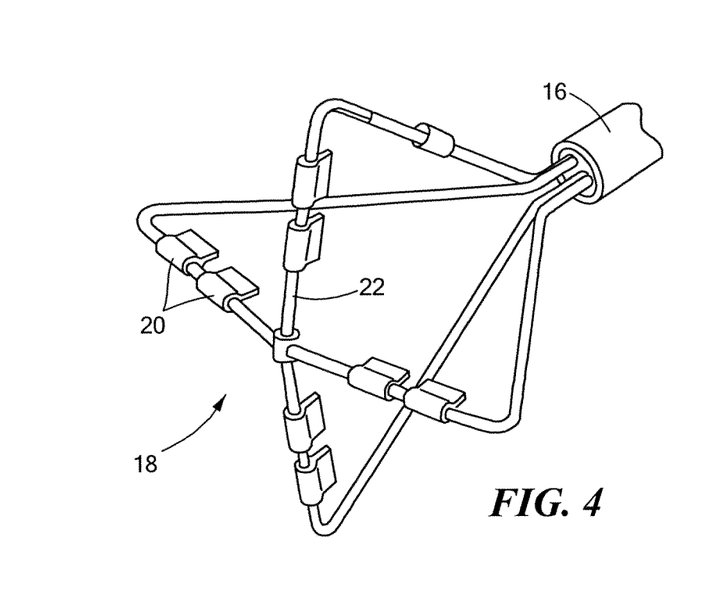
FIG. 4 is an illustration of still another example of an electrode configuration for use with the medical system of FIG. 1.
Figure 5:
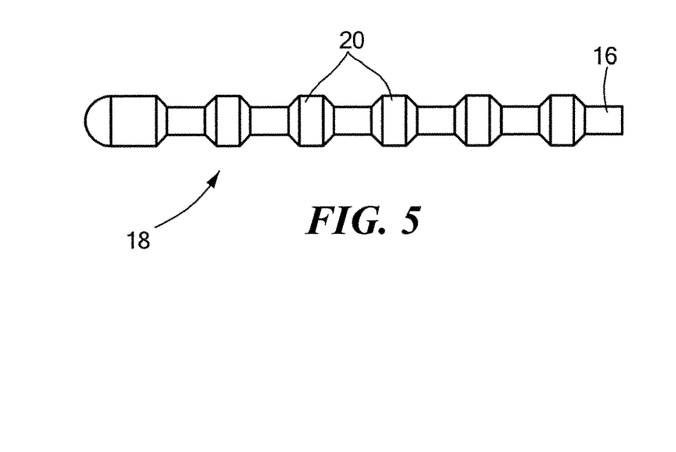
FIG. 5 is an illustration of yet another example of an electrode configuration for use with the medical system of FIG. 1.
Figure 6:
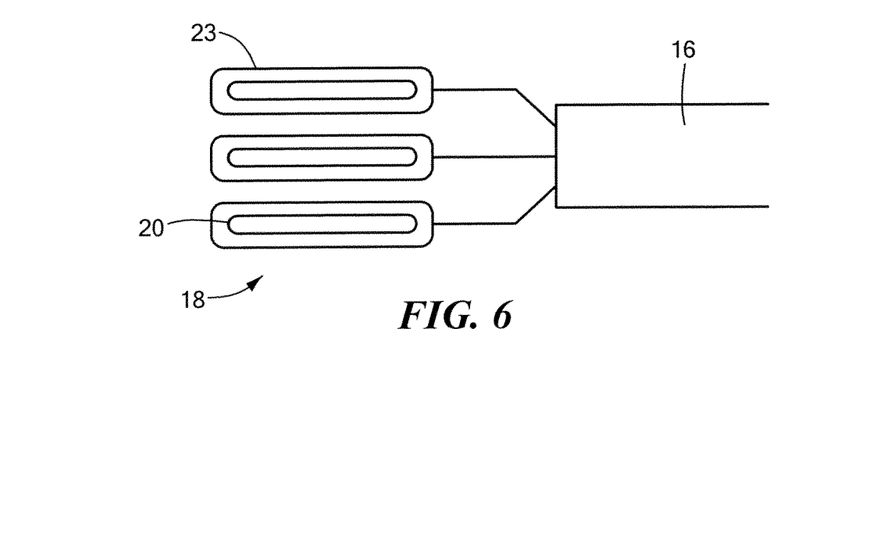
FIG. 6 is an illustration of another example of an electrode configuration for use with the medical system of FIG. 1.
Figure 7:
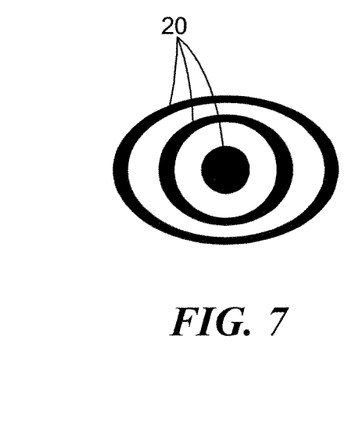
FIG. 7 is an end view of still another example of an electrode configuration for use with the medical system of FIG. 1.

The treatment assemblies of the medical device 12 may deliver, for example, radiofrequency energy or other energetic transfer with a tissue area in proximity to the treatment region(s), such as cardiac tissue. In particular, the medical device 12 may include one or more electrically-conductive segments or electrodes 20 positioned on or about the elongate body 16 for conveying an electrical signal, current, or voltage to a designated tissue region and/or for measuring, recording, or otherwise assessing one or more electrical activities, properties or characteristics of surrounding tissue. The electrodes 20 may be configured in a myriad of different geometric configurations or controllably deployable shapes, and may also vary in number to suit a particular application, targeted tissue structure or physiological feature. For example, as shown in FIG. 2, the electrodes 20 may include an electrode array configurable into a looped or substantially circular configuration. The electrodes 20 in the medical device 12 shown in FIG. 3 are disposed on a plurality of arms 22, with the electrodes 20 positioned in a proximal-facing direction or orientation on the arms 22. FIG. 4 includes a plurality of extendable or deployable arms 22 having a plurality of electrodes 20 in a square-like or "X"-shaped configuration. Turning to FIG. 5, a plurality of electrodes 20 are shown in a substantially linear array extending along a portion of the elongate body 16 of the medical device 12. FIG. 6 illustrates an electrode array having three, elongated electrodes 20 arranged in a substantially parallel arrangement, substantially side-by-side to each other. In FIG. 7, an end view (such as a distal-to-proximal view, for example) of the electrodes 20 is shown. The electrodes 20 may be arranged in a substantially concentric configuration positionable against a tissue region, and the electrodes 20 may be used to for varying combinations of monopolar and/or bipolar energy delivery, as described in more detail below.

The medical device may include one or more sheaths or pods 23 encapsulating or otherwise surrounding at least a portion of one or more of the electrodes 20. For example, as shown in FIG. 6, a pod 23 substantially surrounds a portion of each electrode 20. The pod 23 can facilitate anchoring or positioning of the electrode 20 with respect to a tissue segment. For example, the pod 23 may be in fluid communication with a vacuum or suction source (not shown) of the control unit 14, for example. The electrode 20 may be exposed to the tissue on an underside of the pod 23, such that when the electrode 20 is placed against the tissue, the vacuum-induce pod 23 seals or anchors the electrode against the tissue. The pod 23 may further be in fluid communication with a fluid source (not shown), such as saline, that circulates within the pod 23 to cool the electrode 20 during use. By providing fluid delivery, the pod 23 facilitates lower operating temperatures of the electrode, and further contains any such delivered fluid to prevent unwanted electrical shorting between two electrodes through the delivered fluid.

Additional details related to the configurations, manipulation, and exemplary uses of medical device 12 features and electrode configurations are provided in U.S. patent application Ser. No. 12/116,753, filed on May 7, 2008, entitled "Ablation Therapy System and Method for Treating Continuous Atrial Fibrillation," the entirety of which is hereby incorporated by reference.

Irrespective of the particular geometry or configuration of the treatment assemblies of the medical device 12, each electrode 20 may be electrically coupled to an individually controllable channel 24 of a radiofrequency signal generator 26 of the control unit 14. The independent control of each channel 24 allows a unique, programmable power delivery signal to be sent to each electrode of the attached medical device 12. The independent control of each output channel 24 further allows unique (independent) closed loop power delivery, such as power delivery regulated by tissue temperature information received from one or more temperature sensors integral to the attached medical device 12 and/or from sensors included in a separate device. For example, each electrode 20 may include a sensor, such as a thermocouple, an electrical conductivity sensor, a spectrometer, a pressure sensor, a fluid flow sensor, a pH sensor, and/or a thermal sensor (not shown) coupled to or in communication with the electrodes 20. The sensors may also be in communication with a feedback feature of the control unit 14 to trigger or actuate changes in operation when predetermined sequences, properties, or measurements are attained or exceeded.

The radiofrequency generator 26 may be operable in one or more modes of operation, including for example: (i) bipolar energy delivery between at least two electrodes 20 on the medical device 12 within a patient's body, (ii) monopolar or unipolar energy delivery between one or more of the electrodes 20 on the medical device 12 within a patient's body and a patient return or ground electrode 28 spaced apart from the electrodes 20 of the medical device 12, such as on a patient's skin for example, and (iii) a combination of the monopolar and bipolar modes. The signal provided by the radiofrequency generator 26 may be substantially continuous or include duty cycles of on/off periods of energy delivery. The control unit 14 may include one or more controllers, processors, and/or software modules containing instructions or algorithms to provide for the automated operation and performance of the features, sequences, calculations, or procedures described herein. Additional details related to the configurations and exemplary uses of the radiofrequency signal generator 26 are provided in U.S. patent application Ser. No. 12/117,596, filed on May 8, 2008, entitled "RF Energy Delivery System 10 and Method," the entirety of which is hereby incorporated by reference.

Referring again to FIG. 1, the control unit 14 may include a user interface 30 for the entry, control, and/or monitoring of one or more operational parameters of the system 10. The interface 30 may include a touch screen display, a keypad or other user input components integral to or separate from a housing of control unit 14 (e.g., a separate remote control configuration is contemplated) to allow an operator to input system parameter and output configuration information including but not limited to: electrode selection; power delivery settings/parameters, temperature target(s); and other information. The user interface 30 may also include user output components such as text and/or graphic display screens, indicator lights and other user output components to provide information to the operator, such as visual and audible information including but not limited to electrode selection, power delivery parameters and other information.

Turning now to FIGS. 8-12, the system 10 may be used to treat a selected target tissue region, such as a portion of a heart 32. In particular, the treatment region(s) on the distal portion 18 of the medical device 12 may be used to diagnose or monitor the heart 32, coupled with thermally treating the heart 32 with the electrodes 20. Primarily, the distal portion 18 of the medical device 12 may be positioned into proximity to the targeted tissue region to be diagnosed and/or treated. Such positioning may be aided or facilitated by visualization methods including fluoroscopy or the like as known in the art. The tissue region may include an epicardial segment of the heart 32 believed to be the source of an arrhythmia or other undesirable condition. An epicardial approach may include using one of either a subxiphoid approach or a thoracotomy approach, for example. Each of these methods provides surgical access to an epicardial surface of the heart, as well as allowing subsequent positioning and insertion into the left atrium for diagnosis or treatment if so desired.

Figure 8:
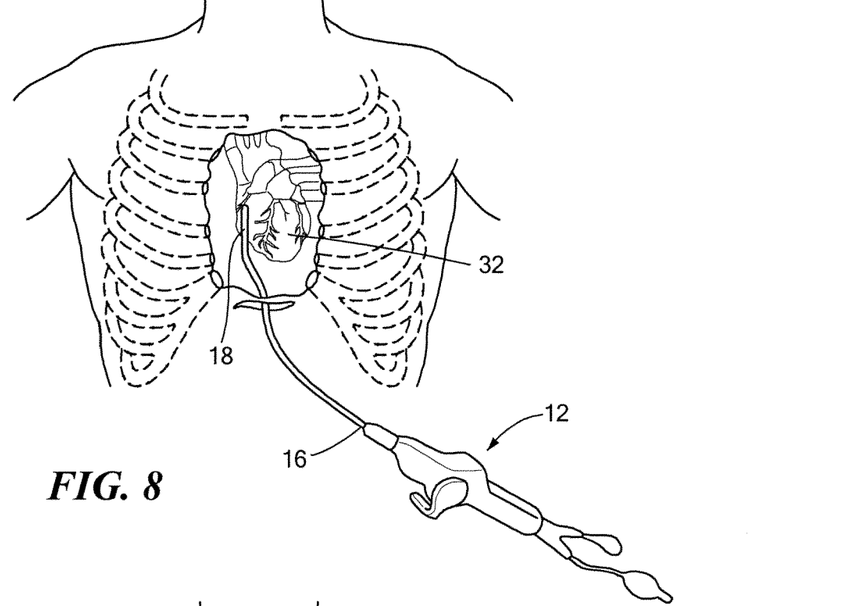
FIG. 8 is an illustration of an exemplary use of a medical device in accordance with principles of the present invention.

Now referring to FIG. 8, employing a subxiphoid technique, the heart 32 may initially be accessed through a puncture technique using a Tuohy needle. A subxiphoid incision, which is typically less than 10 centimeters in length, may be created. As the needle approaches the heart under fluoroscopic guidance or other imaging modality, small amounts of contrast media may be injected to document penetration of the needle tip as it progresses towards the heart. Once properly positioned as indicated by the assistance of medical imaging, a guide wire may be passed through the needle. As a result, a standard introducer sheath, and subsequently the medical device 12, may be passed into a position in proximity to the heart.

Figure 9:
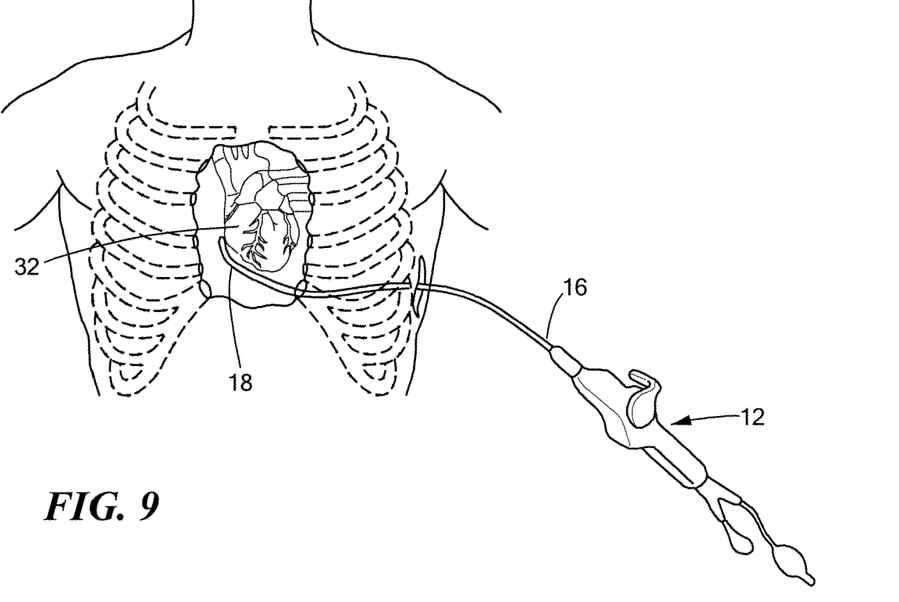
FIG. 9 is an illustration of another exemplary use of a medical device in accordance with principles of the present invention.

Now referring to FIG. 9, a thoracotomy technique may also be performed for providing access the heart. One or more small thoracotomy incisions are made in the chest wall between the ribs to permit access for thoracoscopic instruments and cameras, which provide dissection and visualization capabilities in the pericardial space for insertion and manipulation of medical instruments, such as the medical device 12. The small thoracotomy incisions are typically less than 10 centimeters in length.

In order to ease the use of the medical device 12 in a minimally-invasive surgical approach, the length of a portion of the elongate body 16 may be reduced from that of a typical catheter inserted routed through the femoral artery or other insertion point distant from the heart. Furthermore, the flexibility of the portions of the medical device 12 may be altered in order to provide increased malleability in order to facilitate the accurate positioning of the distal treatment assembly about the heart. Alternatively, pull-wires or other deflection mechanisms can be integrated with or otherwise coupled with the medical device 12 for steering and/or positioning, as is known in the art.

The medical device 12 may also be used to diagnose and/or treat an interior region of the heart 32, such as a septal wall. In such a case, the medical device 12 may be routed intravenously through the femoral artery or other vascular pathway leading to the targeted tissue site.

Once the distal portion 18 or treatment assembly of the medical device 12 is in the desired position, the medical device 12 may be used to measure or assess a property, behavior, or characteristic of the tissue. For example, the electrodes 20 of the medical device 12 may be used to monitor or record an electrical activity of the tissue area indicative of an aberrant electrical pathway or arrhythmia. The electrodes 20 may also be used to measure impedance or other electrical property of the tissue to assess or determine contact with the tissue, or to identify the location of previously-treated tissue regions.

The system 10 may then be operated to thermally affect the targeted tissue. In particular, one or more of the electrodes 20 of the medical device 12 may be used to conduct an electrical current or radiofrequency signal through the targeted tissue site to ablate the problematic tissue. Powering of the electrodes 20 may include delivery of a radiofrequency signal or current from the radiofrequency signal generator 26 resulting in a current flow, and thus heating, between one or more of the electrodes 20 either between each other (e.g., bipolar RF delivery) or to a ground/patient electrode (not shown) in unipolar or monopolar operation. The medical device 12 may be powered ablate or otherwise treat tissue until a preselected temperature or power delivery threshold has been reached. A predefined temperature or power delivery threshold may be selected to ensure that the affected tissue is not charred or otherwise heated to an undesirable degree.

In a particular example, a plurality of the electrodes 20 may be positioned adjacent to or in contact with a tissue segment or region 34. Now referring to FIG. 10, the plurality of electrodes 20 of the medical device 12 may include a first electrode 36, a second electrode 38, and a third electrode 40. The first, second, and third electrodes may constitute part of the electrode array or configurations shown in FIGS. 2-6, for example. The first and third electrodes 36, 40 may substantially surround or otherwise be positioned on opposite sides of the second electrode 38. In the substantially concentric configuration of FIG. 7, the first electrode may be the inner-most electrode, the third electrode being the outer-most electrode, and the second electrode in between the first and third, for example.

Figure 10:
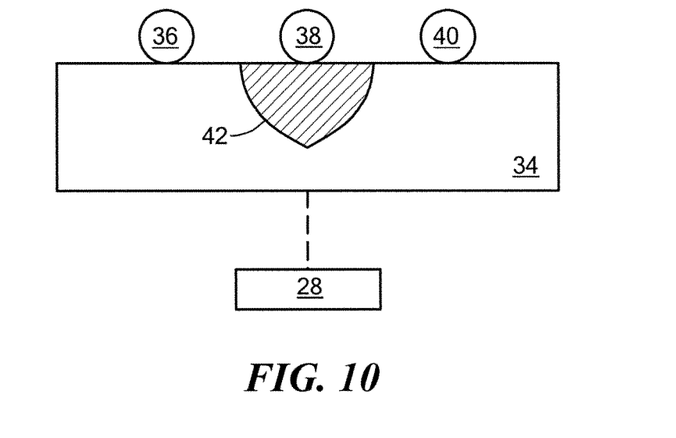
FIGS. 10-12 illustrate an exemplary treatment method for a medical device in accordance with principles of the present invention.

One of the electrodes may initially be operated in a monopolar mode such that an electrical current is conducted between the powered electrode and the return electrode 28 located away from the tissue site, such as on the skin of a patient. For example, the second electrode 38 may be powered by the radiofrequency signal generator 26 to establish an electrical current between the second electrode 38 and the return electrode 28. During the operation of the second electrode 38 and the radiofrequency signal generator 26, a temperature may be measured at or near the second electrode 38, with the measured temperature conveyed to the control unit 14 for analysis. This analysis or measurement may form a basis for modifying a power delivery parameter or timing from the radiofrequency signal generator 26 to achieve a resulting, desired treatment effect on the tissue site, including the formation of a first ablated tissue zone or lesion 42 in the immediate vicinity of the second electrode 38 having a particular depth or dimension.

Figure 11:
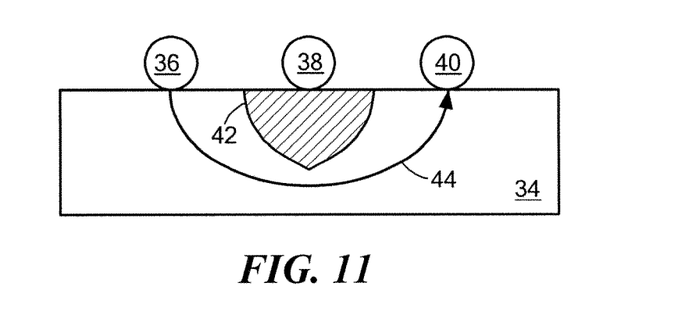
Figure 12:
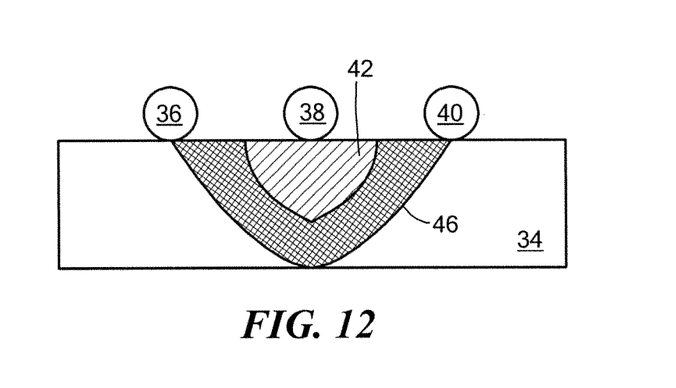

Upon achieving the desired result with the monopolar operation of the second electrode 38, the first and third electrodes 36, 40 straddling or otherwise positioned opposite one another about the second electrode 38 may be operated in bipolar mode to increase the depth and area of treatment, as shown in FIGS. 11-12. For example, the radiofrequency signal generator 26 may deliver a signal or current to the first and/or third electrodes 36, 40 such that current flows between the two electrodes. Electrical conduction through the previously-treated tissue 42 in between the first and third electrodes 36, 40 is significantly reduced or altogether eliminated, and accordingly, electrical current paths 44 between the first and third electrodes 36, 40 flow around the already-ablated tissue region 42, thus driving the current paths deeper into the targeted tissue area to form a secondary ablation lesion or region 46 that is substantially surrounds and/or is continuous with the first ablation region or lesion 42. The secondary ablation zone or region 46 can thus extend from the first ablation zone 42 outward to extend the overall depth and/or width of total treatment area.

By controllably increasing the power delivery or duration parameters of either of the monopolar or bipolar operations, increased tissue depths can be initially ablated, thus driving the subsequent bipolar current paths even deeper into the target tissue region, resulting in a deeper, potentially more effective tissue lesion or ablation site. The above-described system and methods take advantage of the electrical isolation property of ablated tissue, by having a secondary tier of ablation or treatment between an electrode pair straddling or surrounding the initially-operated electrode(s) to force the provided radiofrequency energy to travel deeper into the periphery of the previously-ablated tissue, thus promoting deeper tissue destruction and ablation. The monopolar/bipolar operation of the selected electrodes may be performed sequentially, with the monopolar or initial ablation phase being initially completed prior to initiation of the secondary ablation phase. Alternatively, a time period of monopolar operation may be cyclically alternated or pulsed with a time period of bipolar operation to gradually extend or increase the affected treatment area.

While FIGS. 10-12 illustrate three electrodes 20, it is contemplated the methods described herein can be implemented into a device having numerous electrodes 20, with sequential monopolar-bipolar operations occurring in multiples and/or in various combinations across an electrode array or assembly. Moreover, while the creation of the first ablation zone or lesion has been described using monopolar delivery between a single electrode and the return electrode, it is also contemplated that a bipolar operation of two or more electrodes 20 may be used to form the initial ablation zone, with the subsequent, secondary treatment including electrodes 20 straddling or otherwise positioned opposite on either side of the initially-created ablation lesion.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of treating tissue, comprising:
ablating a first tissue region with a first portion of a medical device placed in contact with a surface of the tissue, the medical device including a plurality of arms, the first portion of the medical device including a first electrode, ablating the first tissue region including conducting an electrical current between the medical device and a return electrode separate from the medical device; and
then ablating a second tissue region with a second portion of the medical device placed in contact with the surface of the tissue, the second tissue region substantially surrounding and being substantially continuous with the first tissue region, the first tissue region having a first tissue depth and the second tissue region having a second tissue depth that is greater than the first tissue depth, the second portion of the medical device including a second electrode and a third electrode, ablating the second tissue region including conducting an electrical current between the second electrode and the third electrode.

2. The method of claim 1, the method further comprising positioning the first electrode in proximity to the first tissue region and positioning the second and third electrodes in proximity to the second tissue region.

3. The method of claim 1, wherein the plurality of arms are extendable.

4. The method of claim 1, wherein the plurality of arms includes a first arm, a second arm, and a third arm.

5. The method of claim 4, wherein each of the first, second, and third arms includes a distal portion and a proximal portion.

6. The method of claim 5, wherein the first electrode is on the proximal portion of one of the first arm, the second arm, and the third arm.

7. The method of claim 1, wherein the plurality of arms includes four arms, each arm having a proximal portion and a distal portion.

8. The method of claim 7, wherein the first electrode, second electrode, and third electrode are on the distal portion of one of the four arms.

9. A method of treating tissue, comprising:
- positioning a first electrode, a second electrode, and a third electrode of a medical device in contact with a same surface of the tissue;
- ablating a first tissue region by conducting an electrical current between the first electrode on a medical device and a return electrode separate from the medical device; and
- then ablating a second tissue region by conducting an electrical current between the second electrode on the medical device and the third electrode on the medical device,
- wherein ablating the first tissue region creates a first lesion having a first tissue depth and ablating the second tissue region creates a second lesion having a second tissue depth, the second lesion being at least substantially continuous with the first lesion and the second tissue depth being greater than the first tissue depth, the second lesion at least substantially surrounding the first lesion.

* * * * *